United States Patent
Yamasawa

[11] Patent Number: 5,218,966
[45] Date of Patent: Jun. 15, 1993

[54] ELECTRONIC BLOOD PRESSURE METER

[75] Inventor: Tsutomu Yamasawa, Takatsuki, Japan

[73] Assignees: Omron Tateisi Electronics Co., Kyoto; Isao Kai, Kameoka, both of Japan

[21] Appl. No.: 810,440

[22] Filed: Dec. 19, 1991

Related U.S. Application Data

[63] Continuation of Ser. No. 639,776, Jan. 14, 1991, abandoned, which is a continuation of Ser. No. 453,263, Dec. 21, 1989, abandoned, which is a continuation of Ser. No. 204,746, Jun. 10, 1988, abandoned.

[30] Foreign Application Priority Data

Jun. 12, 1987 [JP] Japan .................. 62-147387

[51] Int. Cl.$^5$ .................. A61B 5/02
[52] U.S. Cl. .................. 128/677; 128/667; 128/778; 128/681; 128/686
[58] Field of Search .................. 128/664–667, 128/677–688, 672, 633, 689

[56] References Cited

U.S. PATENT DOCUMENTS

| | | | |
|---|---|---|---|
| 3,229,685 | 1/1966 | Ringkamp et al. | 128/667 |
| 3,482,565 | 12/1969 | Gowen | 128/667 |
| 4,621,643 | 11/1986 | New, Jr. et al. | 128/666 X |
| 4,771,790 | 9/1988 | Yamasawa et al. | 128/686 |
| 4,844,084 | 7/1989 | Yamasawa | 128/681 |
| 5,002,061 | 3/1991 | Close et al. | 128/677 |
| 5,025,793 | 6/1991 | Richley et al. | 128/677 |

FOREIGN PATENT DOCUMENTS

61-234841 4/1985 Japan.

Primary Examiner—Lee S. Cohen
Assistant Examiner—K. M. Pfaffle
Attorney, Agent, or Firm—Fish & Richardson

[57] ABSTRACT

In an electronic blood pressure meter for measuring blood pressure from a finger, there is provided a photoelectric sensor including a light emitting element and a light receiving element for detecting pulse wave components from a finger placed in a cuff. Since the variation of the DC component of the pulse wave from one person to another may exceed the linear range of pulse wave measurement, the brightness level of the light emitting element is adjusted according to the level of the DC component contained in the output from the light receiving element. Thereby, favorable extraction of the variational component of the pulse wave is made always within an accurate range of pulse wave measurement.

14 Claims, 9 Drawing Sheets

ELECTRONIC BLOOD PRESSURE METER

This application is a continuation of U.S. application Ser. No. 07/639,776, filed Jan. 14, 1991, now abandoned, which is a continuation of U.S. application Ser. No. 07/453,263, filed Dec. 21, 1989, now abandoned, which is a continuation of U.S. application Ser. No. 07/204,746, filed Jun. 10, 1988, now abandoned.

TECHNICAL FIELD

The present invention relates to an electronic blood pressure meter for measuring blood pressure values from a finger and in particular to such an electronic blood pressure meter having improved photoelectric means for detecting pulse wave.

BACKGROUND OF THE INVENTION

In an electronic blood pressure meter for detecting blood pressure values from a finger, the finger is, first of all, placed in a finger cuff for applying pressure to the finger, and blood pressure values are then computed from the change in the amplitude of pulse wave obtained from the finger as the cuff pressure is gradually reduced, according to a certain algorithm applied to a series of pulse wave data. In such an electronic blood pressure meter, pulse wave is typically detected with a photoelectric sensor including a light emitting element for projecting light onto the finger and a light receiving element for receiving the light reflected from the finger. When blood flow in the finger is in an interrupted state, the reflected light received by the light receiving element consists of a DC signal or, in other words, has a constant level. On the other hand, as the cuff pressure is gradually reduced and blood starts flowing through finger arteries, the volume of the arteries changes and the reflected light accordingly undergoes a pulsating change. Thus, the signal obtained by the light receiving element comprises a DC component and a pulsating AC component superimposed thereon. In an electronic blood pressure meter, a pulse wave component is extracted from the output of the light receiving element and it is used as an important parameter in determining blood pressure values.

Since various properties of a finger, such as color, diameter, the distance between skin surface and arteries, texture, etc. differ a great deal from one person to another and the reflected light obtained by the light receiving element, in particular its DC component accordingly varies to a large extent. Therefore, the individual variation of the DC component may exceed the linear range of the pulse wave detecting means. In other words, the output of the light receiving element may saturate if the amplitude of the reflected light is too large, but the S/N ratio may be excessively small if the amplitude of the reflected light is too small. In either case, a satisfactory measurement of blood pressure is not possible

BRIEF SUMMARY OF THE INVENTION

In view of such problems of the prior art, a primary object of the present invention is to provide an electronic blood pressure meter for a finger having a photoelectric pulse wave detecting means which is adapted to different properties of the finger.

A second object of the present invention is to provide an electronic blood pressure meter having a photoelectric pulse wave detecting means which is capable of a high SN ratio measurement in most conditions.

A third object of the present invention is to provide an electronic blood pressure meter having a photoelectric pulse wave detecting means which is capable of always adapting itself to a measurement in its linear range.

These and other objects of the present invention can be accomplished by providing an electronic blood pressure meter for measuring blood pressure from a finger, comprising: a cuff for receiving a finger therein, provided with an inflatable air chamber; means for supplying pressurized air into the air chamber of the cuff; cuff pressure varying means for varing a pressure of the cuff; a pressure sensor for detecting the pressure of the cuff; photoelectric sensor means comprising a light emitting element for projecting light upon the finger placed in the cuff and a light receiving element for receiving light reflected from the finger; pulse wave extracting means for extracting a pulse wave component from output from the light receiving element; and blood pressure value determining means for determining a blood pressure value from outputs from the pulse wave extracting means and the pressure sensor; further comprising: DC level detecting means means for detecting a DC level of the output from the light receiving element; brightness adjusting means for adjusting a brightness level of the light emitting element according to the DC level detected by the DC level detecting means.

In this electronic blood pressure meter, the level detecting means detects the DC level of the signal received by the light receiving element. When the intensity of the reflected light is high and the DC component is therefore small, the intensity of the light emitted from the light emitting element is increased. Conversely, when the intensity of the reflected light is low and the DC component is therefore large, the intensity of the light emitted from the light emitting element is decreased. Thus, an appropriate DC level is obtained at all time.

According to a certain aspect of the present invention, additionally provided are means for detecting a finger placed in the cuff, and control means for activating the DC level detecting means and the brightness adjusting means after a step of detecting a finger in the cuff and before a step of detecting pulse wave from the finger.

Thus, the adjustment of the brightness level of the light emitting element is performed as a part of an automated process of blood pressure measurement without unduly increasing the time required for blood pressure measurement.

According to another aspect of the present invention, the brightness adjusting means is adapted to adjust the brightness level of the light emitting element when the DC level detected by the DC level detecting means has exceeded a tolerance range there of defined by an upper limit and a lower limit. This simplifies the implementation of the means for adjusting the brightness level of the light emitting element.

Preferably, there is provided means for rapidly venting the cuff and restarting a step of inflating the cuff when the brightness adjusting means has failed to bring the DC level detected by the DC level detecting means within the tolerance range thereof. This again permits execution of an automated process of blood pressure measurement without unduly increasing the time required for blood pressure measurement.

Thus, according to the present invention, even though the variation of the DC component of the pulse wave from one person to another may exceed the linear range of pulse wave measurement, accurate measurement results are always assured since the brightness level of the light emitting element is adjusted according to the level of the DC component contained in the output from the light receiving element. As a result, favorable extraction of the variational component of the pulse wave is made always within an accurate range of pulse wave measurement.

BRIEF DESCRIPTION OF THE DRAWINGS

Now the present invention is described in the following with reference to the appended drawings, in which:

FIG. 3b is a sectional view of the finger cuff shown in FIG. 1a;

DESCRIPTION OF THE PREFERRED EMBODIMENT

Figure 1:
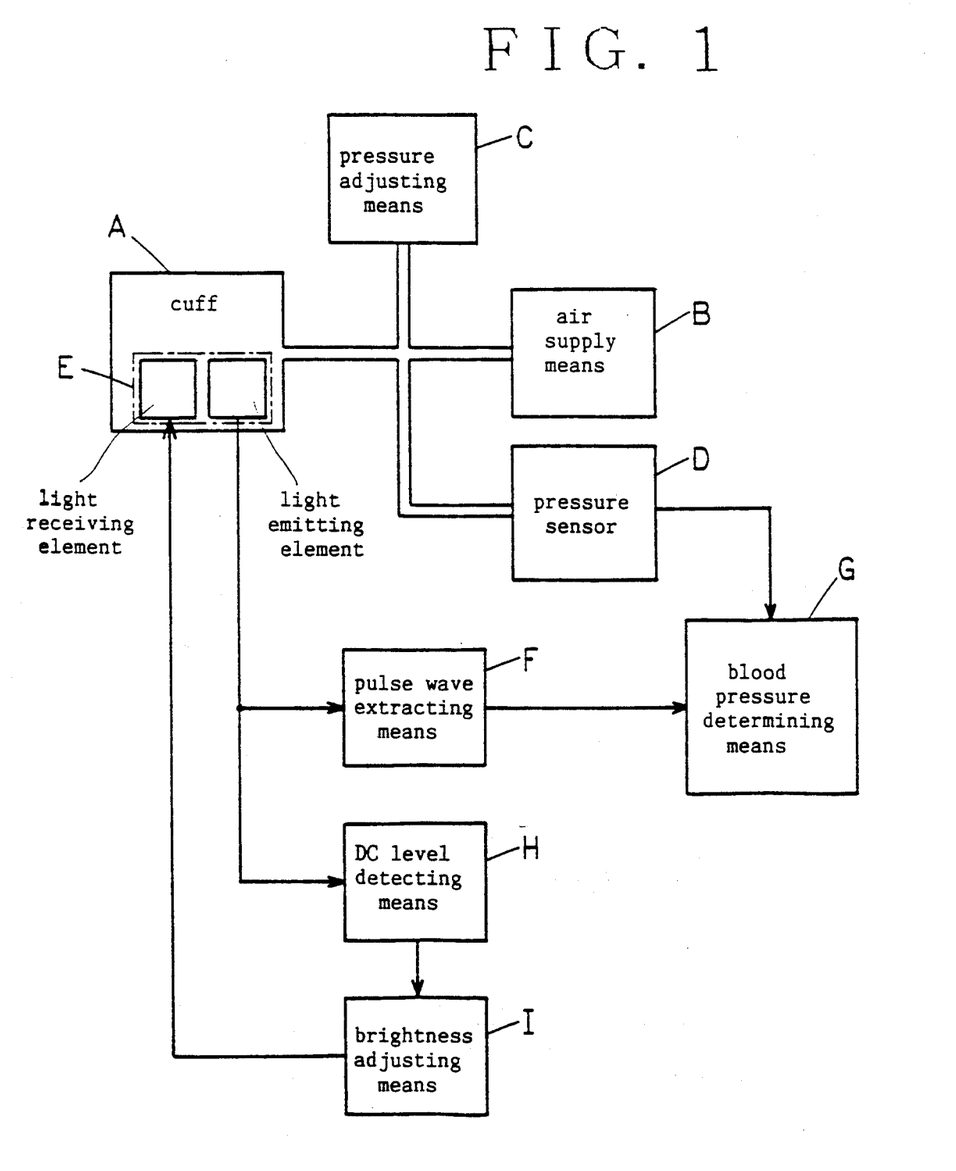
FIG. 1 is a block diagram of a first embodiment of the electronic blood pressure meter according to the present invention.
Figure 2:
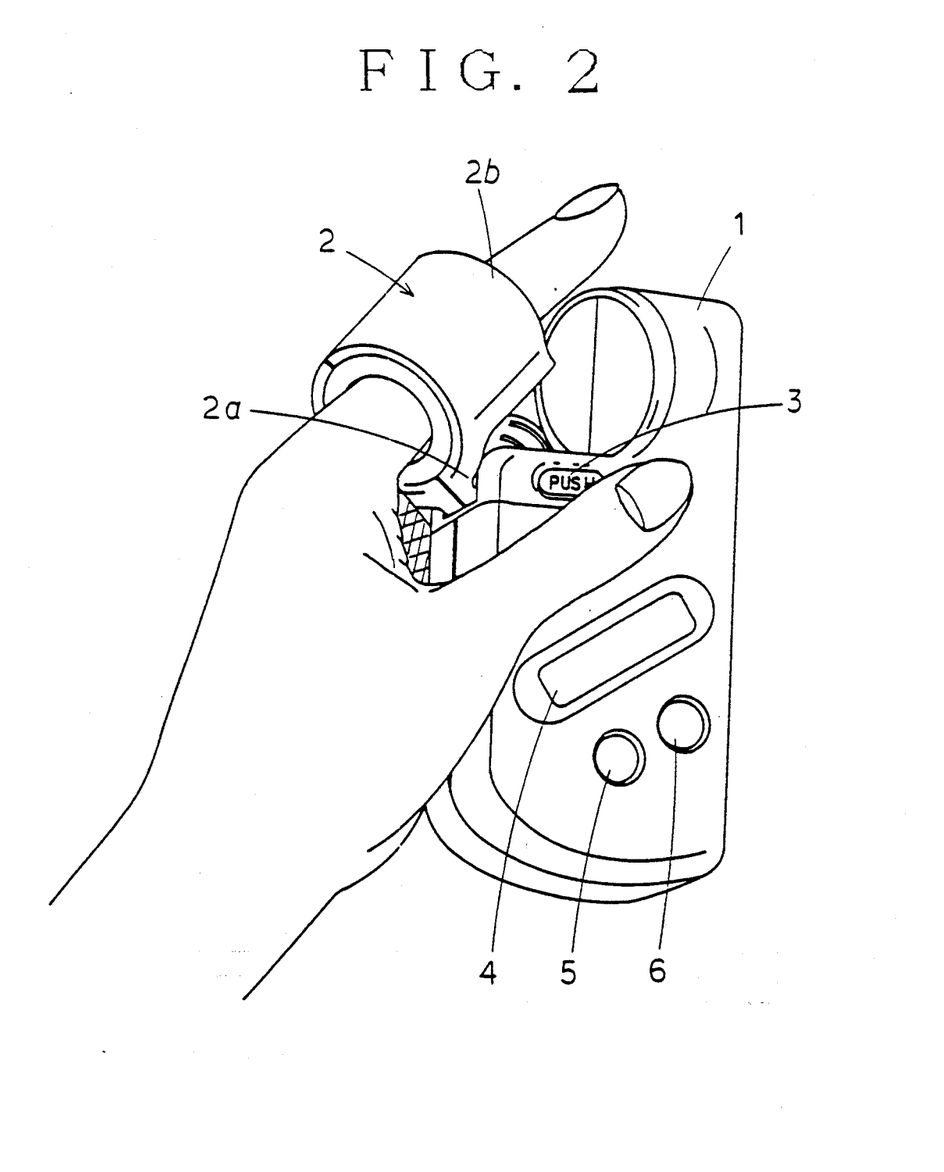
FIG. 2 is an overall perspective view of an electronic blood pressure meter for a finger showing how a finger is placed in the finger cuff of the present invention.

FIG. 2 is an external perspective view of an embodiment of the electronic blood pressure meter for a finger according to the present invention. This electronic blood pressure meter comprises a casing 1 having a finger cuff 2 pivotally attached thereto by way of a pivot mount 2a so that the finger cuff 2 may be rotated with respect to the casing 1 over a certain angle. The main part 2b of the finger cuff 2 may be pivoted away from the casing 1 when a push-button 3 is pressed so as to facilitate placing of a finger therein. The outer surface of the casing 1 is provided with a display unit 4, a power button switch 5 and a start button switch 6. The casing 1 is internally provided with an electronic circuit unit, a motor-driven pump and batteries as described hereinafter.

Figure 3A:
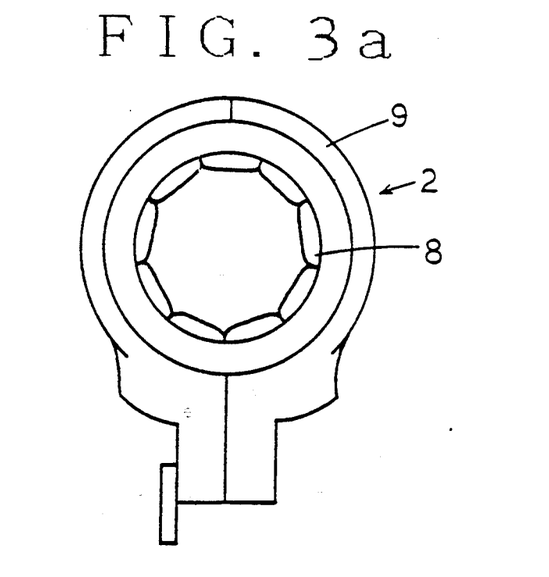
FIG. 3a is a front view of a finger cuff for electronically measuring blood pressure according to the present invention.
Figure 3B:
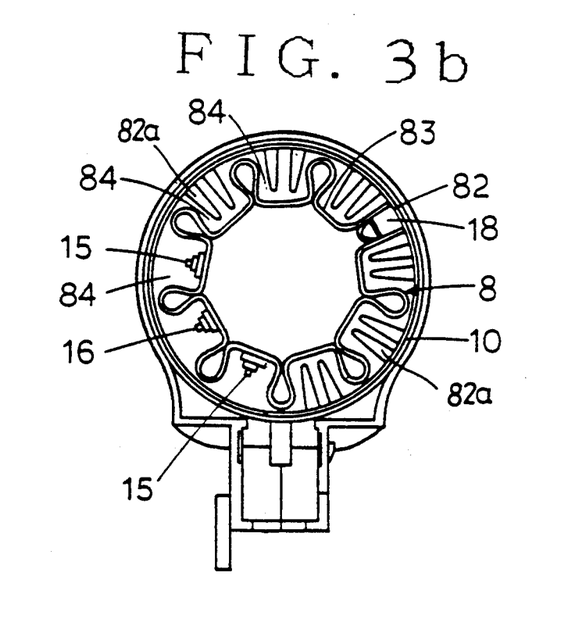

The finger cuff 2 comprises a cylindrical sleeve 10 and a cuff band 8 placed therein, and a cuff holder 9 comprising a pair of hollow semi-cylindrical clamps surrounding the sleeve 10 as shown in FIGS. 3a and 3b. The cuff band 8 comprises a strip of rubber base sheet 82, and a bag skin 83 bonded over the base sheet 82 so as to define a plurality air chambers 84 therebetween at equal interval along a circumferential direction. A light receiving element 16 is placed in one of the air chambers 84 while a pair of light emitting elements 15 are placed in the air chambers located on either side of the air chamber 84 accommodating the light receiving element 16 for the purpose of detecting pulse wave. These elements 15 and 16 are connected to the main circuit unit by way of lead wires not shown in the drawings. The air chambers 84 are communicated with the motor-driven pump in the casing 1 by way of a tube which is not shown in the drawings. Numeral 82a denote projections which are integrally formed with the base sheet 82 for guiding the finger substantially through a central part of the interior of the finger cuff 2.

Two light emitting elements 15 are used here instead of one so as to minimize any fluctuation in the results of pulse wave detection. An additional light receiving element 18 is placed in the inner circumferential surface of the sleeve 10 diagonally opposite to the other light receiving element 16 for the purpose of detecting an insertion of a finger into the finger cuff 2.

Here, it is possible to replace the light emitting elements 15 and the light receiving element 16 with light receiving elements and a light emitting element, respectively.

Figure 4:
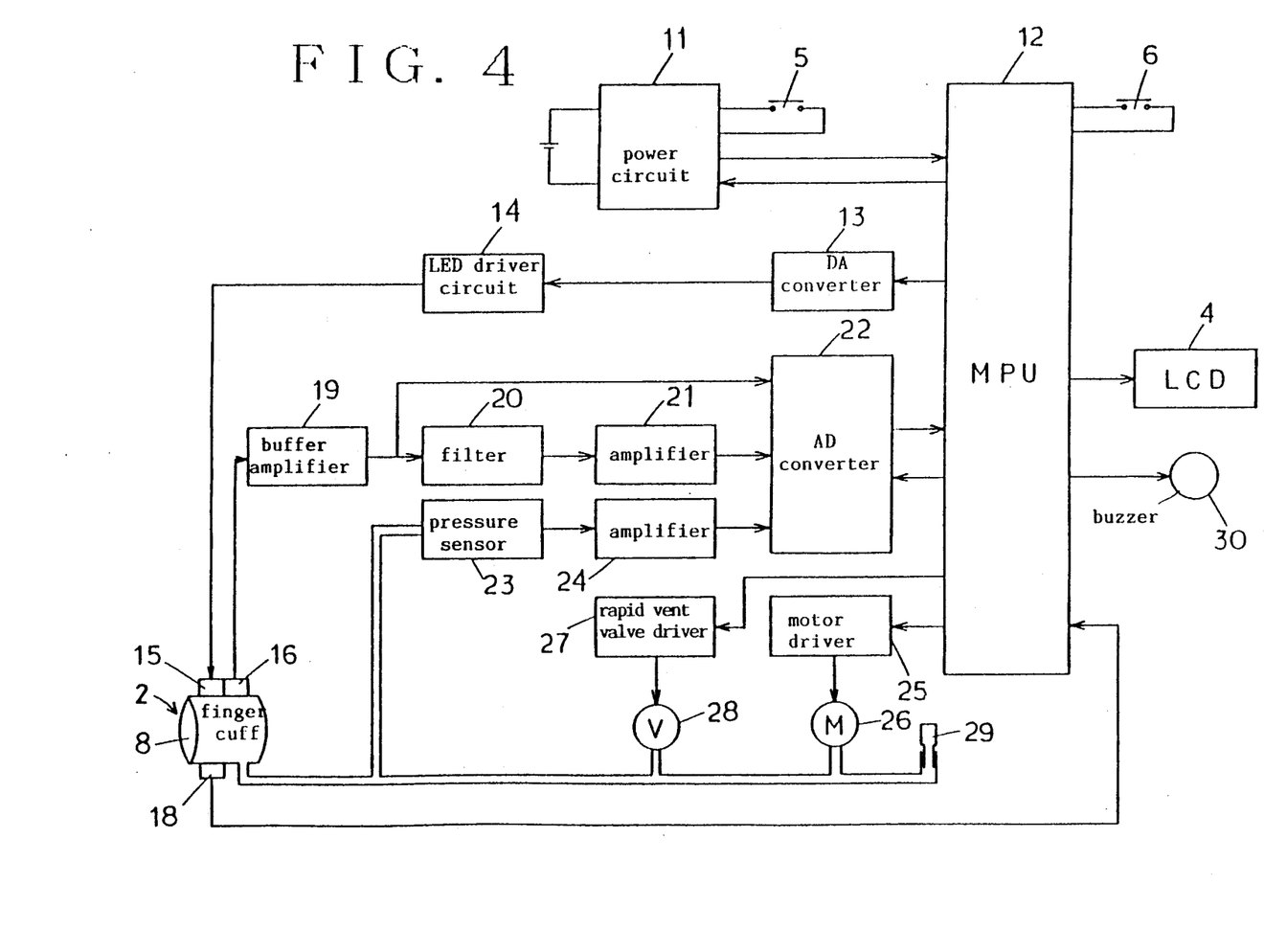
FIG. 4 is a circuit block diagram of the main circuit unit of the electronic blood pressure meter shown in FIG. 2.

FIG. 4 is a block diagram of the main circuit unit. When the power switch 5 is turned on, electric power is supplied to an MPU 12 and other parts of the circuit from a power source circuit 11. The MPU 12 activates a motor 26 by way of a motor driver circuit 25 to pressurize the finger cuff band 8 and vents the cuff band 8 by opening a valve 28 through a rapid vent valve driver circuit 27 to rapidly vent the pressurized air in the cuff band 8 as required. Pulse wave detection is carried out by the MPU 12 as the air chambers 84 are vented through a slow vent valve 29.

Further, a digital signal for determining the level of the brightness of the light emitting elements 15 is produced by the MPU 12, and the digital signal is converted into an analog signal by a DA converter 13. Output of the DA converter 13 is in turn supplied to an LED driver circuit 14 to illuminate the light emitting elements 15 at a selected brightness level. In this embodiment, the light emitting elements 15 can emit light in five different brightness levels according to the bit pattern of the digital control signal set up in the MPU 12. This is to compensate the differences in the amount of reflected light received by the light receiving element 16 from one subject person to another.

Figure 7:
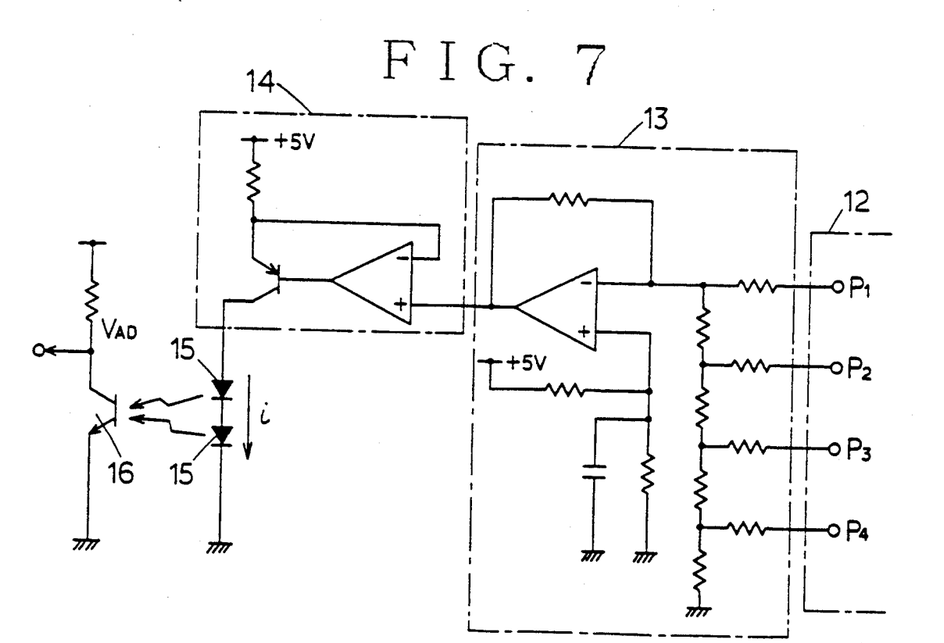
FIG. 7 is a circuit diagram showing specific examples of the DA converter, the LED driver circuit and the photoelectric sensor.

FIG. 7 shows an example of a circuit comprising the DA converter 13, the LED driver circuit 14, the light emitting elements 15, and the light receiving element 16. The MPU 12 supplies a four-bit digital signal ($P_1$, $P_2$, $P_3$ and $P_4$) to the DA converter 13 to designate the brightness level of the light emitting elements 15 from one of five different levels. The DA converter converts the digital signal into a corresponding analog signal, and the LED driver circuit 14 delivers a drive current i corresponding to the analog signal to the light emitting elements 15. The greater the drive current i, the higher the brightness level of the light receiving elements 15 becomes. The correspondence between the logical states of $P_1$, $P_2$, $P_3$ and $P_4$ and the drive current i is given in the following table.

| i (mA) | $P_1$ | $P_2$ | $P_3$ | $P_4$ |
| --- | --- | --- | --- | --- |
| 0 | L | L | L | L |
| 1.25 | L | L | L | H |
| 2.5 | L | L | H | L |
| 5.0 | L | H | L | L |
| 10 | H | L | L | L |

| i (mA) | $P_1$ | $P_2$ | $P_3$ | $P_4$ |
|---|---|---|---|---|
| 20 | H | H | H | H |

As the drive current i is increased, the brightness level of the light emitting elements 15 increases and so does the amount of light received by the light receiving element 16. This in turn causes a larger photoelectric current flowing through the light receiving element 16 and a lower DC component $V_{AD}$ of the pulse wave. Conversely, as the drive current is reduced and the brightness level of the light emitting elements 15 decreases, the amount of the light received by the light receiving element and, therefore, the photoelectric current flowing through the light receiving element 16 increases and the DC component of the pulse wave $V_{AD}$ becomes higher.

The pressure of the finger cuff 2 is detected by a semiconductor pressure sensor 23 and output from the pressure sensor 23 is supplied to the MPU 12 to be stored therein, by way of an amplifier 24 and an AD converter 22. Meanwhile, output from the light receiving element 16 is supplied to the MPU 12 by way of a buffer amplifier circuit 19, a filter circuit 20, an amplifier 21 and the AD converter 22, or directly from the buffer amplifier 19 through the AD converter 22. The direct path through the AD converter 22 from the light receiving element 16 and the buffer amplifier circuit 19 to the MPU 12 is provided for the purpose of obtaining the DC component of the output from the light receiving element 16. The MPU 12 adjusts the brightness level of the light emitting elements 15 according to this DC component. Output from the light receiving element 18 for detecting presence of a finger in the finger cuff 2 is also supplied to the MPU 12.

Basically, the MPU 12 generally performs the various signal processing functions to determine a systolic and a diastolic blood pressure value and displays these blood pressure values on the display unit 4. Further, to notify various states of the electronic blood pressure meter to the user, a buzzer 30 is activated by the MPU 12 as required.

Now the operation of the electronic blood pressure meter for a finger is described in the following with reference to the flow charts of FIGS. 5a through 5d.

Figure 5A:
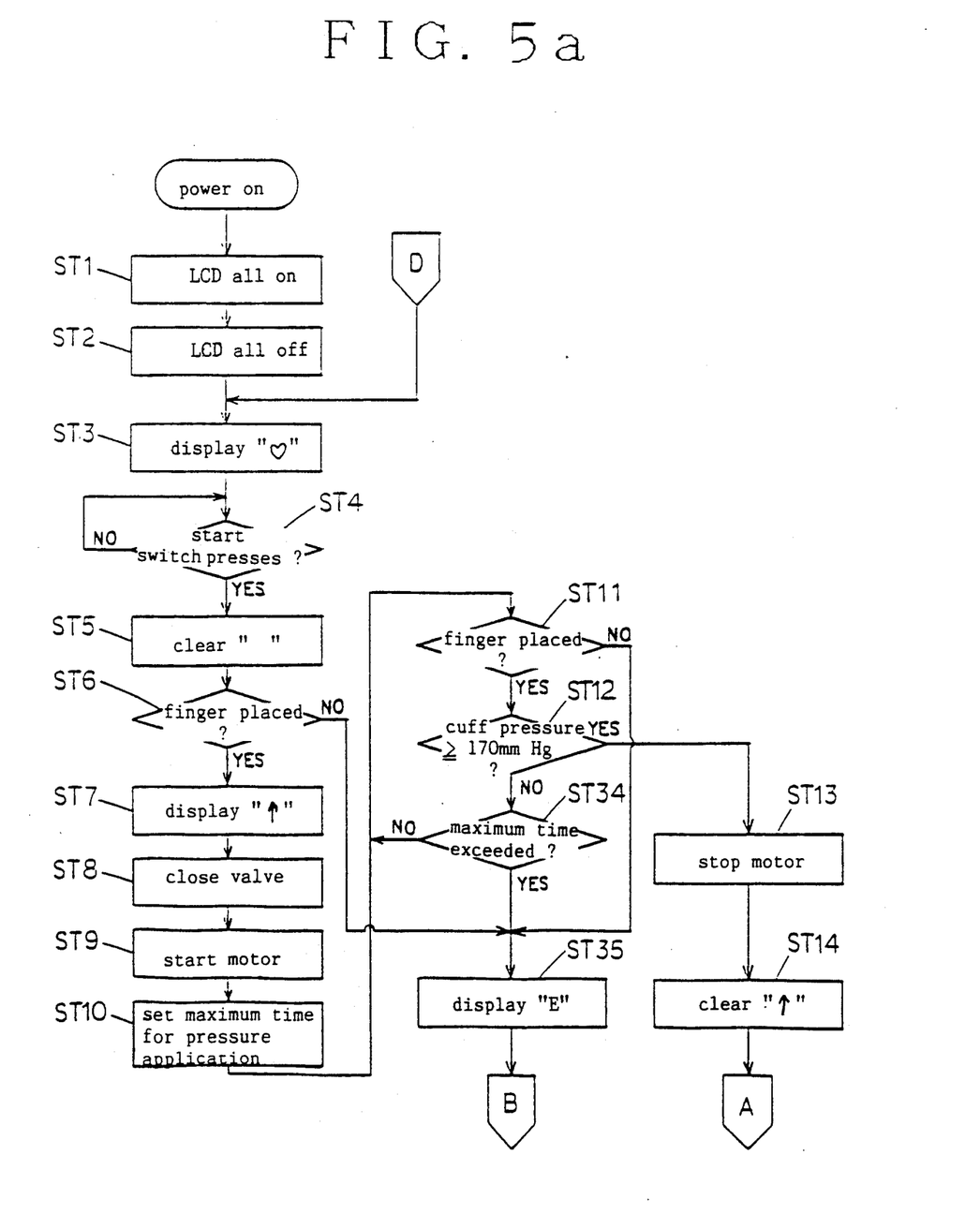
FIGS. 5a through 5d are flow charts showing the operation of the electronic blood pressure meter shown in FIGS. 2 and 3.

When the power switch 5 is turned on, the MPU 12 lights up all the segments in the display unit 4 (ST1) and then turns off all the segments in the display unit 4 (ST2) to test the display unit 4. Then, a heart mark is displayed on the display unit 4 (ST3) to indicate the state of the readiness of the main circuit unit of the electronic blood pressure meter.

When the user presses the start switch 6 in this state, the determination result of ST4 becomes affirmative and the heart mark displayed on the display unit 4 is cleared (ST5). (The determination result of ST4 remains negative and the system stays in this step indefinitely until the start switch 6 is pressed.) It is then determined whether a finer has been placed in the finger cuff 2 or not (ST6). This determination process is carried out by determining whether the light directed to the light receiving element 18 has been interrupted or not. In other words, when the user has placed his finger into the finger cuff 2, the finer prevents the light from being emitted from the light emitting elements 15 and it is detected by the light receiving element 16 as an interruption of light. If a finger has indeed been placed in the cuff 2 as shown in FIG. 2, the determination result of ST6 becomes affirmative and an upward directed arrow is displayed on the display unit 4 (ST7). This arrow mark indicates the beginning of the action of pressurizing the cuff band 8 and the valve 28 is closed at the same time (ST8).

Subsequently, the motor driver circuit 25 is activated to drive the motor-driven pump (ST9). Then, the maximum time interval for pressure application is set up (ST10). After the pressurization of the cuff is started, it is determined again whether the finger is still placed in the finger cuff 2 or not (ST11). If the finger is still placed in he finger cuff 2, the process of pressurization is continued. It is then determined whether the cuff pressure has reached the level of 170 mmHg or not (ST21). If this level has not been reached, it is determined whether the maximum time interval has elapsed or not (ST34). If not, the system flow returns to ST11 and the process of pressurization is continued.

If this target level of pressure has been reached, the system flow advances from SGT12 to ST13 and ST14, and the motor 26 is stopped and the upward arrow displayed on the display unit 4 is cleared. This concludes the process of pressurization.

On the other hand, presence of a finger is not detected in ST6 or ST11, it means that no finger is placed in the cuff and a state of error has occurred. Therefore, "E" is displayed on the display unit 35 and the system flow advances to ST36.

Figure 5B:
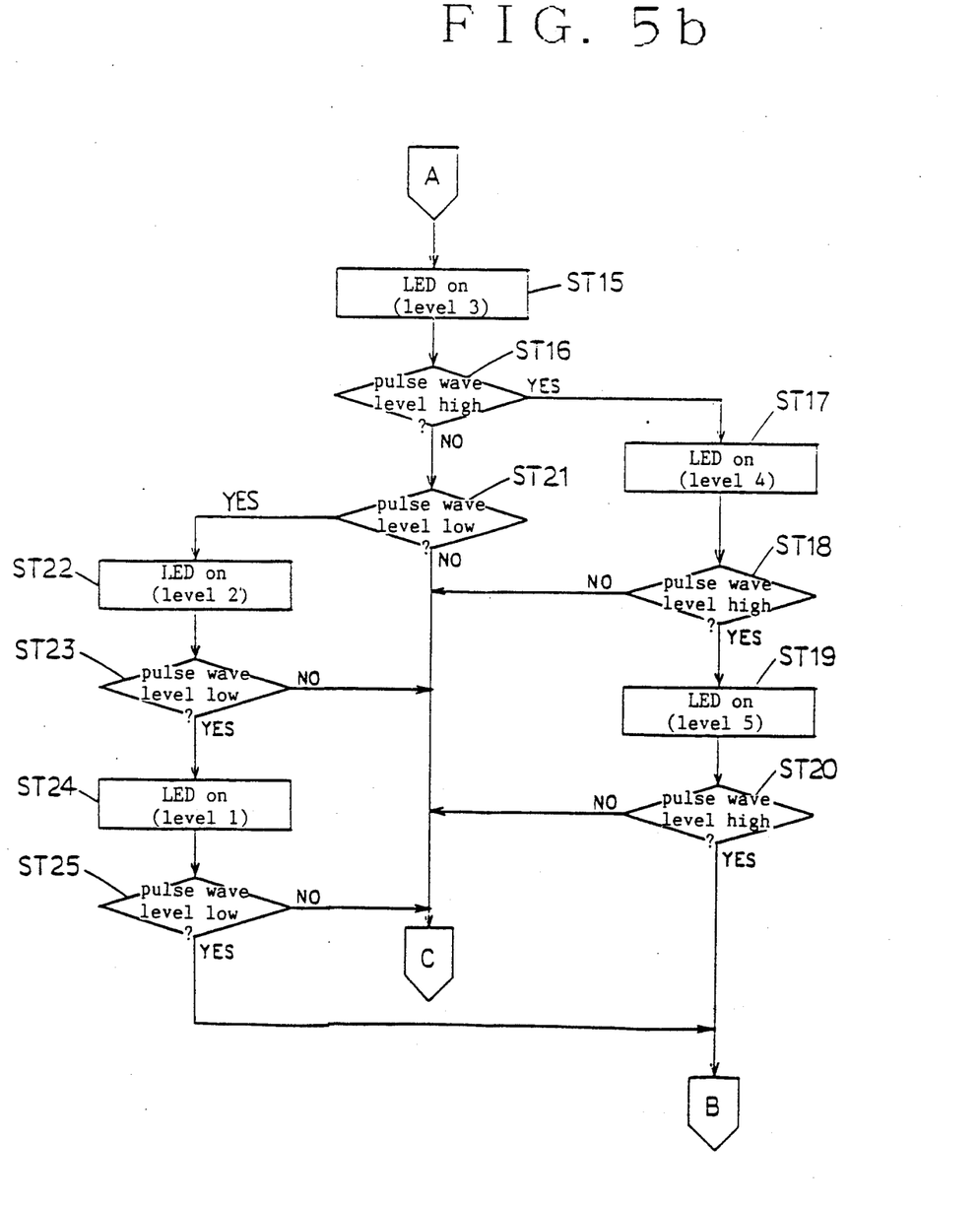

Following ST14, to detect pulse wave, the LED is lighted up at the brightness level of 3 (ST15). It is determined whether the DC component of the pulse wave detected by light receiving element 16 is higher than a certain prescribed value ($V_1$ given in FIG. 6) or not (ST16). If the DC component of the pulse wave is higher than the prescribed value ($V_1$ given in FIG. 6), it means that the amplitude of the reflected light is insufficient and the brightness level is increased by one level or to level 4 (ST17). The brightness level is then evaluated again in ST18 by comparing it with $V_1$ given in FIG. 6 and if the brightness level is still insufficient the brightness is further increased by one more level or to level 5 (ST19). In ST20, the brightness level is evaluated again by comparing it with $V_1$ given in FI. . If the brightness is still insufficient, since there is not any higher brightness level, the system flow advances to ST36. If the brightness level is not insufficient in ST18 or ST20, it means that the brightness level is proper and level 4 or level 5, as the case may be, is maintained thereafter. In these cases, the system flow advances to ST26 in FIG. 5c.

Figure 5C:
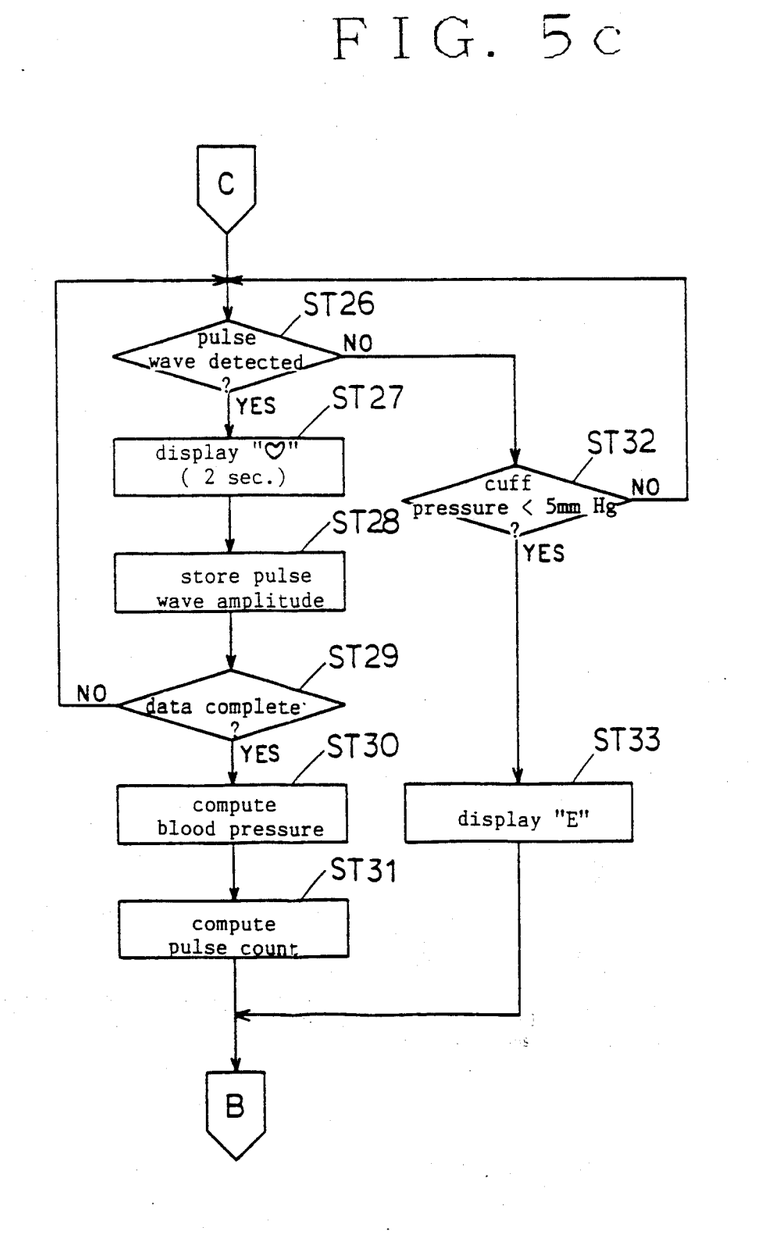
Figure 6:
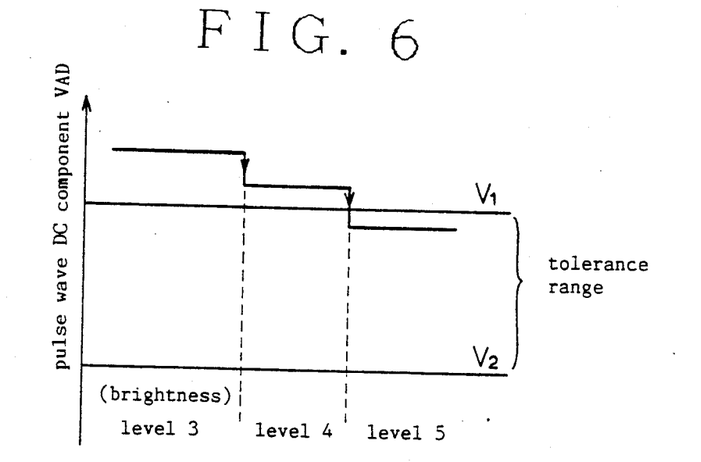
FIG. 6 is a graph for explaining the relationship between the pulse wave level and the brightness level of the light emitting element.

In ST16 or in the state of level 3, if the pulse wave level is not too high, it is then determined in ST21 whether the pulse wave level is too low or not by comparing it with $V_2$ given in FIG. 6. If the pulse wave is not too low, it means that the pulse wave level is in linear range (or between $V_1$ and $V_2$ given in FIG. 6) and the level 3 brightness level is proper. Therefore, the system flow advances to ST26 in FIG. 5c.

On the other hand, if the pulse wave level is found to be too low in ST21, the LED brightness level is reduced to level 2 (ST22) and it is again determined whether the pulse wave level is too low or not in ST23. If it is too low, the system flow advances to ST24 and the LED brightness level is reduced to level 1 and it is again determined whether the LED brightness level is too low or not in ST25. If the brightness level is found to be proper at level 2 or level 1, the LED brightness level is maintained at that level and the system flow advances to ST26 in FIG. 5c.

The steps from ST15 to ST25 shown in FIG. 5b are actually conducted by the MPU 12 as a process of adjusting the brightness level of the light emitting elements 15 to obtain an optimum pulse wave level while a finger is placed in the finger cuff 2. If the pulse wave level is found to be proper, the system flow advances to ST26 shown in FIG. 5c and it is determined whether pulse wave has been detected or not. If the pulse wave has not been detected in ST26, it is determined whether the cuff pressure is equal to or less that 20 mmHg or not in ST32. If no pulse wave has been detected even when the cuff pressure has dropped below 20 mmHg, it is understood as an abnormal state and an error display "E" is made on the display unit 4 in ST33. The system flow then advances to ST36.

If pulse wave is detected in ST26, the heart mark is displayed on the display unit 4 for 0.2 seconds in ST27 and the pulse wave amplitude at that instance is stored in ST28. At this stage, it is determined whether all the data required for computing blood pressure values according to a certain algorithm has been collected or not in ST29. If not, the system flow returns to ST26, and the pulse wave detection is continued until all the data for blood pressure value computation is obtained.

When it is found that all the data has been collected in ST29, blood pressure values are computed in ST30 and a pulse count is computed in ST31. Then, the system flow advances to ST36.

There are a number of algorithms for computing blood pressure values. For instance, the cuff pressure at which a pulse wave amplitude is obtained is determined as a systolic blood pressure and the cuff pressure corresponding to 70% of the maximum pulse wave amplitude is determined as a diastolic blood pressure.

Figure 5D:
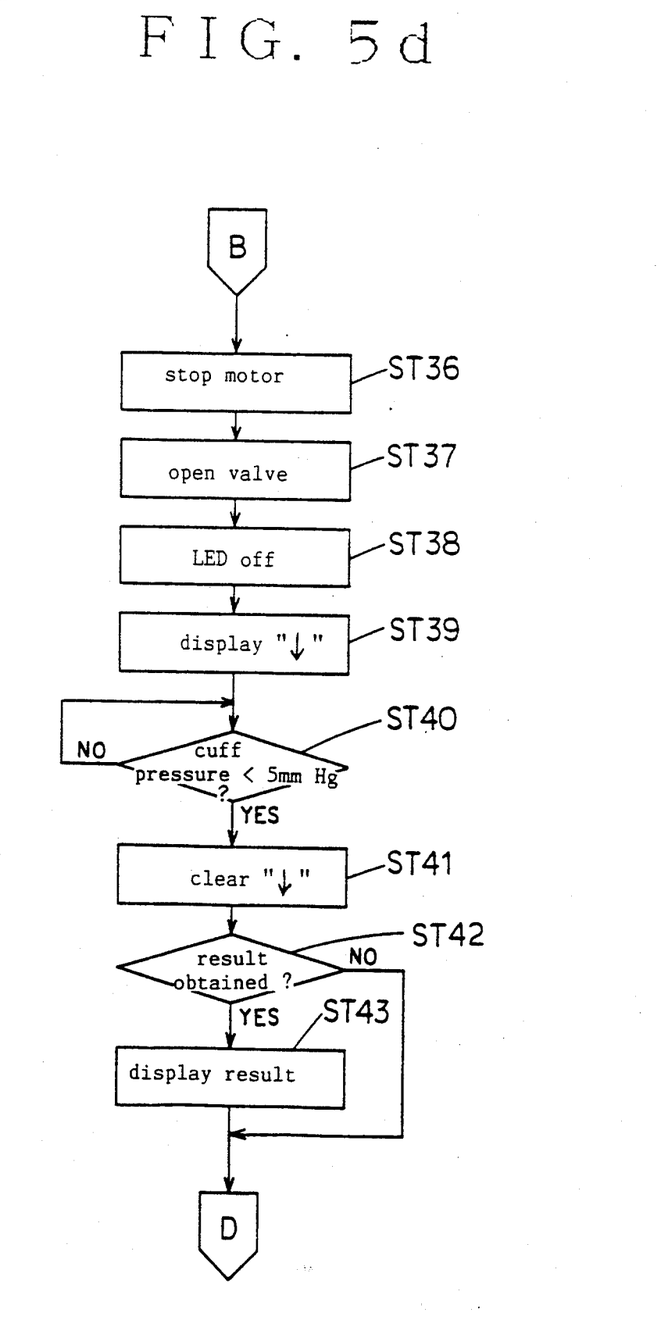

Either when the measurement has been completed or when the measurement was found to be a failure, the motor 26 is stopped in ST36 and the valve 28 is opened to rapidly vent air from the air chambers 34 of the finger cuff 2, followed by clearing of the display on the display unit 4 (ST38) and displaying a downward arrow on the display unit 4 (ST39). The downward arrow represents a rapid venting of the cuff.

When the cuff pressure is found to be equal to or less than 5 mmHg in ST40, the downward arrow is cleared ST41 and it is determined whether a measurement result has been obtained or not in ST42. If a proper measurement result has been obtained, the result is displayed in ST43 and the system flow returns to ST3. If there is no measurement result or a state of error has been detected, the system flow returns to ST3 without any displaying process and the system is made ready for the next measurement process.

Thus, according to the present invention, since the level of the DC component of the output from the light receiving element for detecting pulse wave is detected and the brightness of the light emitting element is adjusted according to this detection result, pulse wave measurement is made possible with an appropriate input DC level for the light receiving element irrespective of the differences in the reflective properties of the fingers of different people. Therefore, the pulse wave component can be with an appropriate sensitivity without the linear range of measurement being exceeded.

Although the present invention has been shown and described with reference to the preferred embodiment thereof, it should not be considered as limited thereby. Various possible modifications and alterations could be conceived of by one skilled in the art to any particular part of the invention without departing from the scope of the invention.

What we claim is:

1. A hand held electronic blood pressure meter, comprising:
    a body portion adapted to be gripped by a thumb and at least one of another finger and a portion of a palm of a single hand;
    a rotatable cuff means for receiving a further finger of the single hand, said cuff means being pivotally disposed on said body portion and being disposed so as to be pivotable by said further finger, said cuff means being pivotally disposed on a pivot which is located on a side of the body portion adjacent the portion of the palm of the single hand;
    means for supplying pressurized air into the cuff means;
    cuff pressure varying means for varing the pressure of the cuff means;
    sensor means for detecting the pressure of the cuff means; and
    blood pressure value determining means for determining a blood pressure value from outputs from the sensor means;
    wherein said hand held electronic blood pressure meter is structured and arranged to be held in and capable of being used by the single hand during operation.

2. A hand held electronic blood pressure meter as defined in claim 1, wherein said cuff means includes a portion which is disposed in a recess formed in said body portion.

3. A hand held electronic blood pressure meter as defined in claim 1, further comprising operational control means for controlling the operation of said electronic blood pressure meter.

4. A hand held electronic blood pressure meter as defined in claim 3, wherein said operational control mans is disposed on a further side of said body portion and is arranged on said body portion so as to be capable of being actuated by the thumb of the single hand.

5. A hand held electronic blood pressure meter as defined in claim 4, wherein said operational control means includes a power switch and a start/stop switch.

6. A hand held electronic blood pressure meter as defined in claim 3, wherein said visual display means is disposed on a further side of said body portion.

7. A hand held electronic blood pressure meter as defined in claim 1, further comprising visual display means for outputting a visual signal indicative of the blood pressure volume of the single hand.

8. A hand held electronic blood pressure meter as determined in claim 6, further comprising:
    pivot control means for controlling the pivoting action of said cuff means;
    operational control means for controlling the operation of said electronic blood pressure meter;
    visual display means for outputting a visual signal indicative of the blood pressure value of the single hand; and
    wherein said pivot control means, said operational control means and said visual display means are disposed on a further side of said body portion and said pivot control means and said operational control means are arranged on said body portion so as to be capable of being actuated by the thumb of the single hand.

9. A hand held electronic blood pressure meter according to claim 1, wherein said sensor means is a photoelectric sensor.

10. A hand held electronic blood pressure meter according to claim 1, wherein said sensor means is a pressure sensor.

11. A hand held electronic blood pressure meter, comprising:
a body portion adapted to e gripped by a thumb and at least one of another finger and a portion of a palm of a single hand;
a rotatable cuff means for receiving a further finger of the single hand, said cuff means being pivotally disposed on said body portion and being disposed so as to be pivotable by said further finger;
pivot control means for controlling the pivoting action of said cuff means,
means for supplying pressurized air into the cuff means;
cuff pressure varying means for varying the pressure of the cuff means;
sensor means for detecting the pressure of the cuff means; and
blood pressure value determining means for determining a blood pressure value from outputs from the sensor means,
wherein said hand held electronic blood pressure meter is structured and arranged to be held in and capable of being used by the single hand during operation.

12. A hand held electronic blood pressure meter as defined in claim 11, wherein said pivot control means is disposed on a further side of said body portion and is arranged on said body portion so as to be capable of being actuated by the thumb of the single hand.

13. A hand held electronic blood pressure meter according to claim 11, wherein said sensor means is a photoelectric sensor.

14. A hand held electronic blood pressure meter according to claim 11, wherein said sensor means is a pressure sensor.

* * * * *